United States Patent
Paul et al.

(10) Patent No.: US 6,780,952 B2
(45) Date of Patent: Aug. 24, 2004

(54) PROCESS FOR MANUFACTURING SILANIZED (METH)ACRYLATES

(75) Inventors: Jean-Michel Paul, Metz (FR); Joseph Rondini, Ham-sous-Varsberg (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 10/189,778

(22) Filed: Jul. 8, 2002

(65) Prior Publication Data

US 2003/0120010 A1 Jun. 26, 2003

(30) Foreign Application Priority Data

Jul. 6, 2001 (FR) .............................. 01 08998

(51) Int. Cl.$^7$ .............................................. C08F 118/04
(52) U.S. Cl. .................................... 526/320; 526/329.7
(58) Field of Search ............................ 526/320, 329.7; 556/442, 446, 411

(56) References Cited

U.S. PATENT DOCUMENTS 4,609,749 A * 9/1986 Kotzsch et al. ............. 556/411

FOREIGN PATENT DOCUMENTS

DE 3443961 6/1986

OTHER PUBLICATIONS

XP002194307—Abstract, Donets, V.G.: "Synthesis of allyl-silyltrimethacrylate" retrieved from STN, (1980).

* cited by examiner

Primary Examiner—Robert D. Harlan

(74) Attorney, Agent, or Firm—Millen, White, Zelano & Branigan, P.C.

(57) ABSTRACT

The silanized (meth)acrylate (I) is manufactured by reacting the anhydride (II) with a silanized compound (III). This process gives a crude mixture containing compound (IV) in addition to compound (I), after which the said mixture may be freed of the lightest compounds by distillation or may be subjected to a distillation to obtain the pure compound (I).

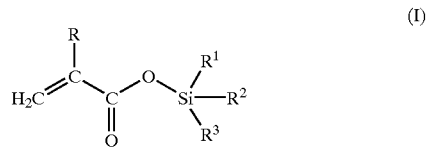

(I)

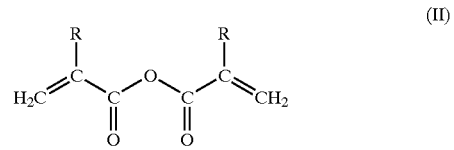

(II)

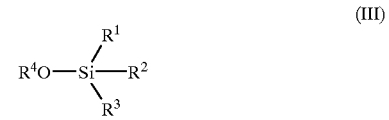

(III)

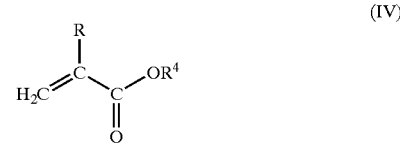

(IV)

R=H or Me; $R^1$, $R^2$, $R^3$=linear or branched $C_1$–$C_{10}$ alkyl, aryl or aralkyl, these radicals possibly being substituted and possibly containing hetero atoms; $R^4$=H or a radical falling within the definition given above for $R^1$, $R^2$ and $R^3$.

21 Claims, No Drawings

PROCESS FOR MANUFACTURING SILANIZED (METH)ACRYLATES

The present invention relates to a process for manufacturing a silanized (meth)acrylate of formula:

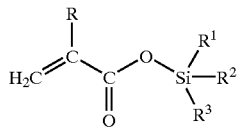

(I)

in which:

R represents hydrogen or methyl;

$R^1$, $R^2$ and $R^3$ each independently represent a linear or branched $C_1$–$C_{10}$ alkyl radical, an aryl radical or an aralkyl radical, these radicals possibly being substituted and possibly containing hetero atoms.

The (meth)acrylates (I) are known for their use as hydrolysable monomers which serve for the preparation of binders in the field of self-smoothing antifouling marine paints intended, for example, for coating the hulls of boats or more generally of materials in contact with a marine environment (U.S. Pat. Nos. 4,593,055 and 4,687,792).

Various synthetic routes are described in the literature for manufacturing these silanized (meth)acrylates. These may be grouped in Table 1 below:

TABLE 1

| | SYNTHETIC ROUTE | DOCUMENTS | DRAWBACKS |
|---|---|---|---|
| 1 | $H_2C=C(R)C(=O)OH$ + $Cl-Si(R^1)(R^2)(R^3)$ in the presence of a tertiary amine | J. Polym. Sci. A1, 8, 319 (1970); Eur. Polym. J. vol. 28, n 4, pages 335–338 (1992); US-A-4 593 055; JP-A-04 342 593; JP-A-04 342 595 | use of chlorosilane, an expensive reagent; formation of a large amount of hydrochloride which is to be separated out by filtration |
| 2 | $H_2C=C(R)C(=O)OH$ + $HO-Si(R^1)(R^2)(R^3)$ in the presence of a $TiCl_4/MgSO_4$ catalyst | JP-A-05 025 188 | formation of a large amount of disiloxane $R^1R^2R^3SiOSiR^1R^2R^3$ |
| 3 | $H_2C=C(R)C(=O)OH$ + $HO-Si(R^1)(R^2)(R^3)$ in the presence of a Pd/C, $Cu_2O$, $H_2PtCl_6$ catalyst | JP-A-04 154 790; JP-A-05 25 187; JP-A-10 195 084; JP-A-10 212 293 | generation of $H_2$ (implementation problem - safety; addition of $H_2$ to the double bond) |
| 4 | $H_2C=C(R)C(=O)OH$ + $Me_3Si-N(H)-SiMe_3$ | Pierce, Silylation of organic compounds (1968); Kashutina, Usp. Khim. 44, 1620 (1975) | synthetic route specific for trimethylsilyl (meth)acrylates |
| 5 | $H_2C=C(R)C(=O)Cl$ + $HO-Si(R^1)(R^2)(R^3)$ | EP-A-0 131 626 | use of (meth)acryloyl chloride; HCl as by-product |
| 6 | $H_2C=C(CH_2)C(=O)OAg$ + $Me_3SiCl$ | Tsuruta, Bull. Inst. Res. Kyoto Univ. 40, 151 (1962); Andreev, Zh. Obschch. Khim. 30, 2782 (1960) | use of Ag salt; solid precipitate to be separated out by filtration |
| 7 | $H_2C=C(CH_3)C(=O)OK$ + $ClSiMe_3$ | Eur. Polym. J. vol. 28, n 4, pages 335–339 (1992) | precipitate of KCl to be separated out by filtration |

R = H, $CH_3$;

R, $R^1$ to $R^3$ as defined above;

Me = methyl;

tBu = tert-butyl

The synthetic routes described in Table 1 present, in one way or another, a number of drawbacks that the Applicant Company has succeeded in overcoming by carrying out the synthesis using (meth)acrylic anhydride and a silanized alkoxylated or hydroxylated derivative.

The process according to the invention for preparing the silanized (meth)acrylates (I) defined above allows them to be obtained under good conditions of conversion, selectivity and production efficiency, without waste products, without separation solids and without generation of $H_2$. Thus, the manufacture of the silanized (meth)acrylates (I) according to the present invention may be carried out in total safety in simple stirred, heated stainless-steel reactors, in contrast with processes which generate $H_2$ or HCl as by-products; in addition, it does not require any labour-intensive individual steps of the type such as filtration, washing or drying of solids.

A first subject of the present invention is thus a process for manufacturing a silanized (meth)acrylate of formula (I), as defined above, characterized in that the anhydride of formula (II):

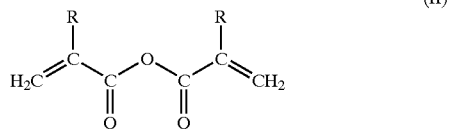

(II)

in which R is as defined above, is reacted with a silanized compound of formula (III)

(III)

in which:
- $R^1$, $R^2$ and $R^3$ are as defined above; and
- $R^4$ represents hydrogen or a radical falling within the definition given above for $R^1$, $R^2$ and $R^3$.

$R^1$, $R^2$, $R^3$ and $R^4$ are chosen especially from methyl, ethyl, n-propyl, isopropyl, n-butyl, isobutyl, tert-butyl, phenyl and alkylphenyl radicals with alkyl being $C_1$–$C_{10}$, $R^4$ also possibly being hydrogen. $R^4$ is preferably chosen from hydrogen, ethyl, n-propyl and n-butyl.

As indicated above, the radicals $R^1$ to $R^3$ may be substituted, for example, with halogen atoms, such as Cl or Br, or groups —$NR^5R^6$ ($R^5$ and R6 representing $C_1$ to $C_8$ alkyl groups); moreover, the chain of these radicals may be interrupted with a hetero atom such as O or S.

The reaction of the invention is generally performed with a compound (II)/compound (III) molar ratio of between 0.3/1 and 3/1, although molar ratios of less than 0.3/1 or greater than 3/1 can theoretically be used. In accordance with one preferred embodiment of the invention, the reaction is performed with a compound (II)/compound (III) molar ratio of between 0.7/1 and 2/1 and preferably between 0.9/1 and 1.2/1.

The reaction is performed at a temperature of from 20 to 200° C., preferably from 75 to 100° C., in particular from 80 to 120° C., and preferably at atmospheric pressure, although it is possible to perform the process under a pressure above or below atmospheric pressure.

Moreover, the reaction is performed to the point of maximum conversion of the reagents, determined using the usual analytical methods, for example such as gas chromatography. The reaction time depends on the operating conditions and on the reagents (II) and (III) used in the synthesis. It is generally between 3 and 8 hours.

The reaction (acylation) may be carried out with or without a catalyst. The use of a catalyst makes it possible to prevent the formation of disiloxanes, to increase the reaction kinetics and, as a result, to reduce the reaction time.

Among the catalysts which may be used, individually or as a mixture of two or more, mention may be made of 1-methylimidazole, dimethylaminopyridine, 4-pyrrolidinopyridine, 4-piperiditriflates, tributylphosphine, triethylamine, pyridine, montmorillonites such as montmorillonite K10 and KSF, protic acids such as para-toluenesulphonic acid and Lewis acids such as $ZnCl_2$, the catalyst(s) generally being used in a proportion of from 0.05 to 1% by weight relative to the mixture of reagents. The use of larger amounts of catalyst is possible, although this does not provide an additional gain in terms of reducing the reaction time. 1-Methylimidazole is the preferred catalyst.

Moreover, the process according to the present invention is generally carried out in the presence of at least one polymerization inhibitor chosen especially from hydroquinone, hydroquinone methyl ether, phenothiazine, 2,2,5,5-tetramethyl-1-pyrrolidinyloxy (TEMPO) and homologues thereof such as 3-carboxy-2,2,5,5-tetramethyl-1-pyrrolidinyloxy, 2,2,6,6-tetramethyl-1-piperidinyloxy, 4-hydroxy-2,2,6,6-tetramethyl-1-piperidinyloxy, 4-methoxy-2,2,6,6-tetramethyl-1-piperidinyloxy and 4-oxo-2,2,6,6-tetramethyl-1-piperidinyloxy, and hindered phenolic inhibitors such as 2,4-dimethyl-6-tert-butylphenol and 2,6-di-tert-butyl-para-cresol, and homologues thereof, the polymerization inhibitors) being used in a proportion of from 0.05 to 0.5% by weight relative to the mixture of reagents.

The reaction according to the invention is advantageously carried out in the presence of air. The end of the reaction is determined by analysing the reaction medium (for example by GC).

The reaction according to the invention gives a crude mixture containing, besides compound (I), the compound of formula (IV) as a by-product:

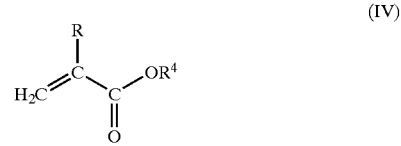

(IV)

in which R and $R^4$ are as defined in Claim 1, after which the said mixture may be freed of the lightest compounds by distillation (topping) or may be subjected, in order to obtain the pure compound (I), to a distillation, generally using a distillation column for the more volatile compounds (I) or a film evaporator for those with the highest boiling points.

The present invention also relates to the use of the crude mixture or of the mixture freed of the lightest compounds or of the pure compound (I), as obtained by the above process, as hydrolysable monomer(s) of a monomer composition whose polymerization gives a binder intended for self-smoothing antifouling marine paints. The binder is generally present in the paint composition in a proportion of from 10 to 30% by weight (in dry form).

The paint composition comprises the other usual ingredients, such as:
- adjuvants, for instance soybean lecithin, modified hydrogenated castor oil or viscosity stabilizers (such as Viscostab CNF 896 manufactured by the company Atofina);
- pigments and fillers, such as non-acicular zinc oxide, cuprous oxide and rutile titanium oxide; and
- solvents and diluents such as the solvent naphtha, toluene and xylene.

The examples which follow illustrate the present invention without, however, limiting its scope. The percentages are expressed on a weight basis except where otherwise mentioned. The abbreviations used are as follows:

| | |
|---|---|
| AMA20 | methacrylic anhydride |
| AA20 | acrylic anhydride |
| AMA | methacrylic acid |
| AA | acrylic acid |
| MAM | methyl methacrylate |
| Bu3SiMA | tributylsilyl methacrylate |
| Bu3SiOSiBu3 | hexabutyldisiloxane |
| MAM | methyl methacrylate |
| Bu3SiOMe | tributylmethoxysilane |
| Bu3SiOH | tributylsilanol |
| Bu3SiH | tributylsilane |
| 1-MIM | 1-methylimidazole (catalyst) |
| BHT | 2,6-di-tert-butyl-para-cresol (polymerization inhibitor) |
| TOPANOL A | 2,4-dimethyl-6-tert-butylphenol (polymerization inhibitor) |
| Me | methyl |
| Et | ethyl |
| nOct | n-octyl |
| isoPro | isopropyl |
| nPro | n-propyl |
| Bu | butyl |
| nBu | n-butyl |
| isoBu | isobutyl |
| tBu | tert-butyl |

EXAMPLE 1

Preparation of Bu3SiMA from AMA20 and Bu3SiOMe

The following ingredients:
43.2 g of 98% pure AMA20;
59.5 g of 97% pure Bu3SiOMe;
0.1 g of TOPANOL A;
0.1 g of BHT; and
0.5 g of 1-MIM,
are introduced into a glass reactor heated by circulation of thermostatically-maintained hot oil inside a jacket, mechanically stirred (stirrer of anchor type), on which is mounted a distillation column of Vigreux type with a head condenser, a reflux head, a vacuum separator and a trapping vessel.

The AMA20/Bu3SiOMe molar ratio is 1.1/1.
Air is bubbled through throughout the syntheses.
The mixture is heated at 110° C. for 5 hours with stirring. At the end of these 5 hours, the degree of conversion of Bu3SiOMe is greater than 96%. The Bu3SiMa content is 74%. The crude product is then distilled under vacuum.

A first head fraction F1 (13.4 g) is collected under a pressure of 26 664.48 to 13 332.24 Pa (200 to 100 mmHg); the fraction is more than 99% composed of MAM.

A fraction F2 (3.5 g) composed of a mixture of AMA20 and AMA is then distilled off.

The Bu3SiMA is distilled off under 533.29 Pa (4 mmHg) (reactor temperature from 140 to 180° C. at the end of the distillation/column head temperature of 138 to 142° C.).

65 g of Bu3SiMa are thus recovered in a purity of 97%. The formation of Bu3SiOSiBu3 is negligible.

EXAMPLES 2 TO 12

Preparation of Silanized (meth)Acrylates by the Reaction of, (meth)Acrylic Anhyride and an Alkoxylated Silanized Compound

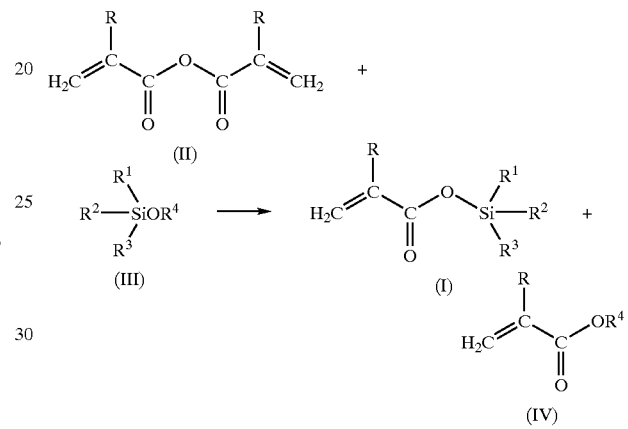

11 different syntheses are performed as in Example 1, but starting in each case:
with AMA20 or AA20 as compound (II) (R representing Me and H, respectively); and
with an alkoxylated silanized compound (III) in which the radicals $R^1$ to $R^4$ are indicated in Table 1.

The said table also shows:
the composition of the reaction medium (in mol %) at the initial time ti and at the time tf of the end of the reaction (after 5 hours at 110° C.);
the degree of conversion DC (%) of compound (III), and the yield Y (%) of compound (I).

TABLE 2

| | | | | | | Composition of the reaction medium (moles/100 g of crude product) | | | | | | | | | |
|---|---|---|---|---|---|---|---|---|---|---|---|---|---|---|---|
| | | | | | | Compound (III) | | Compound (II) | | Compound (IV) | | Compound (I) | | DC | Y |
| Example | R | $R^1$ | $R^2$ | $R^3$ | $R^4$ | ti | tf | ti | tf | ti | tf | ti | tf | (%) | (%) |
| 2 | Me | Me | Me | Me | Me | 0.36 | 0.04 | 0.39 | 0.05 | 0 | 0.32 | 0 | 0.34 | >94 | >99 |
| 3 | Me | Me | Me | nOct | Me | 0.26 | 0.01 | 0.29 | 0.03 | 0 | 0.24 | 0 | 0.26 | >96 | >99 |
| 4 | Me | Me | Me | Me | Et | 0.34 | 0.10 | 0.37 | 0.10 | 0 | 0.25 | 0 | 0.24 | 70 | >99 |
| 5 | Me | Me | Me | Me | nPro | 0.32 | 0.10 | 0.36 | 0.12 | 0 | 0.20 | 0 | 0.23 | 68 | >99 |
| 6 | Me | Me | Me | Me | isoPro | 0.32 | 0.15 | 0.36 | 0.19 | 0 | 0.14 | 0 | 0.17 | 53 | >99 |
| 7 | H | Me | Me | Me | Me | 0.40 | 0.05 | 0.44 | 0.06 | 0 | 0.33 | 0 | 0.33 | 87 | 94 |
| 8 | H | Me | Me | nOct | Me | 0.28 | 0.05 | 0.33 | 0.07 | 0 | 0.22 | 0 | 0.215 | 82 | 93 |
| 9 | H | Bu | Bu | Bu | Me | 0.26 | 0.05 | 0.30 | 0.06 | 0 | 0.19 | 0 | 0.20 | 80 | 95 |
| 10 | H | Me | Me | Me | Et | 0.37 | 0.10 | 0.42 | 0.08 | 0 | 0.26 | 0 | 0.26 | 73 | 96 |
| 11 | H | Me | Me | Me | nPro | 0.35 | 0.07 | 0.40 | 0.08 | 0 | 0.22 | 0 | 0.25 | 80 | 89 |
| 12 | H | Me | Me | Me | isoPro | 0.35 | 0.10 | 0.40 | 0.12 | 0 | 0.18 | 0 | 0.20 | 71 | 80 |

EXAMPLE 13

Preparation of Bu3SiMA from AMA20 and Bu3SiOH

The process was performed as in Example 1, except that Bu3SiOH was used instead of Bu3SiOMe.

The Bu3SiOH used has the following composition by mass (in %):

| | |
|---|---|
| Bu3SiOH | 91.4 |
| Bu3SiOMe | 0.9 |
| Bu3SiOSiBu3 | 2.6 |
| Bu3SiH | 0.9 |
| Others | q.s. 100 |

The AMA20/Bu3SiOR molar ratio is 2/1.

After reaction for 6 hours at 110° C., the crude reaction product has the following composition by mass (in %):

| | |
|---|---|
| MAM | 0.3 |
| AMA | 16.6 |
| AMA20 | 27.4 |
| Bu3SiOH | 0.13 |
| Bu3SiOMe | 0.08 |
| Bu3SiMA | 48 |
| Bu3SiOSiBu3 | 7.9 |

Some of the Bu3SiOH was consumed in the form of Bu3SiOSiBu3; the rest was converted into Bu3SiMA.

What is claimed is:

1. A process for manufacturing a silanized (meth) acrylate of formula I:

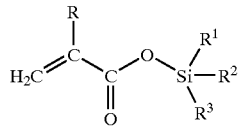

wherein:
R represents hydrogen of methyl;
$R^1$, $R^2$ and $R^3$ each independently represent a linear or branched $C_1$–$C_{10}$ alkyl radical, an aryl radical, an aryl radical or an aralkyl radical, these radicals optionally being substituted and optionally containing hetero atoms
said process comprising reacting an anhydride of formula (II):

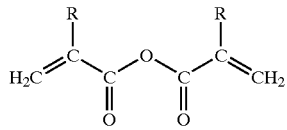

wherein R is as defined above, with silanized compound of formula (III)

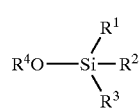

in which:
$R^1$, $R^2$, and $R^3$ are as defined above; and
$R^4$ represents hydrogen or a radical falling within the definition given above for $R^1$, $R^2$ and $R^3$.

2. A process according to claim 1, wherein $R^1$, $R^2$, $R^3$ and $R^4$ are selected from the group consisting of methyl, ethyl, n-propyl, isopropyl, n-butyl, isobutyl, tert-butyl, phenyl and alkylphenyl radicals with alkyl being $C_1$–$C_{10}$, and $R^4$ is optionally hydrogen.

3. A process according to claim 1, wherein the reaction is performed with a compound (II)/compound (III) molar ratio of between 0.3/1 and 3/1.

4. Process according to claim 3, characterized in that the reaction is performed with a compound (II)/compound (III) molar radio of between 0.7/1 and 2/1 and preferably between 0.9/1 and 1.1/1.

5. A process according to claim 1, wherein the reaction is performed at a temperature of from 20 to 200° C.

6. A process according to claim 1, wherein the reaction is performed at atmospheric pressure.

7. A process according to claim 1, wherein the reaction is performed to the point of maximum conversion of the reagents.

8. A process according to claim 7, wherein the reaction is performed for a period of from 3 to 8 hours.

9. A process for manufacturing a silanized (meth) acrylate of formula I:

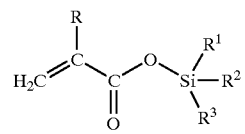

wherein:
R represents hydrogen of methyl:
$R^1$, $R^2$ and $R^3$ each independently represent a linear or branched $C_1$–$C_{10}$ alkyl radical, an aryl radical, an aryl radical or an aralkyl radical, these radicals optionally being substituted and optionally containing hetero atoms
said process comprising reacting an anhydride of formula (II):

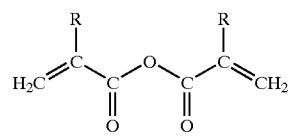

wherein R is as defined above, with silanized compound of formula (III)

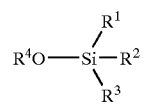

in which:
$R^1$, $R^2$, and $R^3$ are as defined above; and
$R^4$ represents hydrogen or a radical falling within the definition given above for $R^1$, $R^2$ and $R^3$, and wherein the reaction is performed in the presence of at least one catalyst selected from the group consisting of 1-methylimidazole, dimethylamino-pyridine, 4-pyrrolidinopyridine, 4-piperidinopyridine, 4-morpholinopyridine, triflates, tri-butylphosphine, triethylamine, pyridine, mont-morillonites, protic acids and Lewis acids, the catalyst(s) being used in a proportion of from 0.05 to 1% by weight relative to the mixture of reagents.

10. A process according to claim 1, wherein the reaction is carried out in the presence of at least one polymerization inhibitor selected from the group consisting of hydroquinone, hydroquinone methyl ether, phenothiazine, 2,2,5,5-tetramethyl-1-pyrrolidinyloxy and homologues thereof such as 3-carboxy-2,2,5,5-tetramethyl-1-pirrolidinyloxy, 2,2,6,6-tetramethyl-1-piperidinyloxy, 4-hydroxy-2,2,6,6-tetramethyl-1-piperidinyloxy, and 4-methoxy-2,2,6,6-tetramethyl-1;-piperidinyloxy, and hindered phenolic inhibitors, the polymerization inhibitor(s) being used in a proportion of from 0.05 to 0.5% by weight relative to the mixture of reagents.

11. A process according to claim 1, said process producing a crude mixture containing, besides compound (I) a compound of formula (IV):

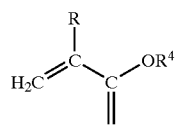

in which R and R$^4$ are as defined in claim 1, said process optionally further comprising freeing said crude mixture of the lightest compounds by distillation or subjecting said oxide mixture to a distillation to obtain the pure compound (I).

12. A crude mixture, or a mixture freed of lightest compounds obtained by the process of claim 11.

13. A self-smoothing antifouling marine paint comprising the crude mixture of claim 12 as hydrolysable monomer(s) of a monomer composition whose polymerization gives a binder.

14. A process according to claim 5 when the reaction is conducted at 75–100° C.

15. A process according to claim 5 when the reaction is conducted at 80–120° C.

16. A process according to claim 9 when the catalyst is paratoluenesulfonic acid or ZnCl$_2$.

17. A process according to claim 8 when the reaction is conducted at 80–120° C.

18. A process according to claim 9 when the reaction is conducted at 80–120° C.

19. A process for manufacturing a silanized (meth) acrylate of formula I:

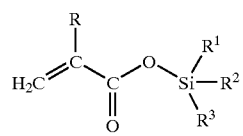

wherein:

R represents hydrogen of methyl;

R$^1$, R$^2$ and R$^3$ each independently represent a linear or branched C$_2$–C$_{10}$ alkyl radical, an aryl radical, an aryl radical or an aralkyl radical, these radicals optionally being substituted and optionally containing hetero atoms said process comprising reacting an anhydride of formula (II):

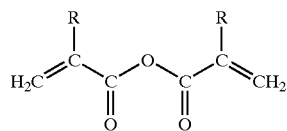

wherein R is as defined above, with silanized compound of formula (III)

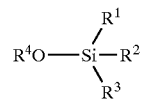

in which:

R$^1$, R$^2$, and R$^3$ are as defined above; and

R$^4$ represents hydrogen or a radical falling within the definition given above for R$^1$, R$^2$ and R$^3$.

20. A process for manufacturing a silanized (meth) acrylate of formula I:

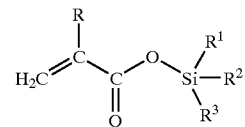

wherein:

R represents hydrogen of methyl;

R$^1$, R$^2$ and R$^3$ each independently represent, an aryl radical, an aryl radical or an aralkyl radical, these radicals optionally being substituted and optionally containing hetero atoms said process comprising reacting an anhydride of formula (II):

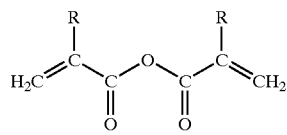

wherein R is as defined above, with silanized compound of formula (III)

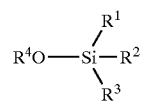

in which:

R$^1$, R$^2$, and R$^3$ are as defined above; and

R$^4$ represents hydrogen or a radical falling within the definition given above for R$^1$, R$^2$ and R$^3$.

21. A crude mixture obtained by the process of claim 11.

* * * * *

UNITED STATES PATENT AND TRADEMARK OFFICE
CERTIFICATE OF CORRECTION

PATENT NO. : 6,780,952 B2
DATED : August 24, 2004
INVENTOR(S) : Jean-Michel Paul et al.

It is certified that error appears in the above-identified patent and that said Letters Patent is hereby corrected as shown below:

Column 8,
Line 11, reads "molar radio" should read -- molar ratio --

Signed and Sealed this

Tenth Day of May, 2005

JON W. DUDAS
*Director of the United States Patent and Trademark Office*